(12) United States Patent
Oka et al.

(10) Patent No.: US 7,641,794 B2
(45) Date of Patent: Jan. 5, 2010

(54) BLOOD PROCESSING FILTER

(75) Inventors: Shin-ichiroh Oka, Oita (JP); Yoshimasa Matsuura, Oita (JP); Tomohisa Yokomizo, Oita (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 1146 days.

(21) Appl. No.: 10/332,569

(22) PCT Filed: Jul. 10, 2001

(86) PCT No.: PCT/JP01/05964

§ 371 (c)(1),
(2), (4) Date: Sep. 29, 2003

(87) PCT Pub. No.: WO02/04045

PCT Pub. Date: Jan. 17, 2002

(65) Prior Publication Data
US 2004/0251195 A1     Dec. 16, 2004

(30) Foreign Application Priority Data
Jul. 10, 2000 (JP) .............................. 2000-208738
Jul. 11, 2000 (JP) .............................. 2000-209811

(51) Int. Cl.
*B01D 36/00* (2006.01)

(52) U.S. Cl. ....................... 210/259; 210/446; 210/450; 210/488; 210/489; 210/506; 210/512.1; 210/257.1; 210/335

(58) Field of Classification Search .................. 210/335, 210/450, 483–485, 488–490, 503–508, 257.1, 210/360.1, 782, 259, 496, 512.1, 446; 494/16–19, 494/31

See application file for complete search history.

(56) References Cited

U.S. PATENT DOCUMENTS

| 4,157,967 | A |   | 6/1979  | Meyst et al. |
| 4,401,567 | A | * | 8/1983  | Shindo et al. .......... 210/500.22 |
| 4,925,572 | A | * | 5/1990  | Pall ............................ 210/767 |
| 5,190,657 | A |   | 3/1993  | Heagle et al. |
| 5,290,449 | A |   | 3/1994  | Heagle et al. |
| 5,456,845 | A | * | 10/1995 | Nishimura et al. .......... 210/782 |
| 5,591,337 | A | * | 1/1997  | Lynn et al. .................. 210/489 |

(Continued)

FOREIGN PATENT DOCUMENTS

EP     0526678 A1    2/1993

(Continued)

OTHER PUBLICATIONS

European Search Report EP 01 94 7947.

(Continued)

*Primary Examiner*—Joseph W Drodge
(74) *Attorney, Agent, or Firm*—Young & Thompson

(57) ABSTRACT

A flexible blood filter allowing smooth flow of a liquid and being excellent in separation resistance, pressure resistance and centrifugation resistance. The blood processing filter, includes a first filter element for removing aggregates from blood, a second filter element for removing leukocytes provided in the downstream of the first filter element, and a third filter element having gas permeability of 3 to 40 cc/cm2/sec per thickness of 1 cm provided between the second filter element and the outlet port. The filter contains a seal zone at a peripheral section which contains five layers including a layer of molten material and layers of molten material mixed with filter element material.

14 Claims, 2 Drawing Sheets

U.S. PATENT DOCUMENTS

| | | | |
|---|---|---|---|
| 5,609,947 A * | 3/1997 | Kamei et al. | 428/212 |
| 5,846,438 A * | 12/1998 | Pall et al. | 210/767 |
| 6,074,869 A * | 6/2000 | Pall et al. | 435/286.5 |
| 6,325,422 B1 * | 12/2001 | Verkaart et al. | 285/93 |
| 6,367,634 B1 * | 4/2002 | Lynn et al. | 210/489 |
| 6,422,397 B1 | 7/2002 | Lynn et al. | |
| 6,497,685 B1 * | 12/2002 | Dennehey et al. | 604/252 |
| 2002/0148764 A1 | 10/2002 | Lynn et al. | |
| 2003/0209479 A1 * | 11/2003 | Lynn et al. | 210/257.1 |
| 2007/0017879 A1 * | 1/2007 | Proulx et al. | 210/767 |

FOREIGN PATENT DOCUMENTS

| | | |
|---|---|---|
| GB | 1571731 A | 7/1980 |
| GB | 2056301 A | 3/1981 |
| JP | 11-216179 | 8/1999 |
| JP | 2001-161812 | 6/2001 |
| WO | WO 95/17236 | 6/1995 |
| WO | WO9517236 | 6/1995 |

OTHER PUBLICATIONS

International Search Report PCT/US94/14819.

* cited by examiner

BLOOD PROCESSING FILTER

TECHNICAL FIELD

The present invention relates to a blood processing filter for removing undesirable components such as aggregate and leukocytes from blood. In particular, the present invention relates to a precise and disposable blood processing filter for removing micro aggregate and leukocytes which may cause side effects from whole blood preparations, erythrocyte preparations, thrombocyte preparations, blood plasma preparations, and the like for blood transfusion.

BACKGROUND ART

Whole blood collected from a donor is used for transfusion, as is, only in rare cases, but is commonly separated into components, such as an erythrocyte preparation, thrombocyte preparation, blood plasma preparation, and the like to be stored for transfusion. Since micro aggregate and leukocytes included in these blood preparations cause various side effects during blood transfusion, there have been increasing occasions wherein these undesirable components are removed before blood transfusion. The need for leukocyte removal has widely been recognized particularly in recent years. Removal of leukocytes from all kinds of blood preparations for blood transfusion before using for transfusion has been legislated in some European countries.

The most common method of removing leukocytes from blood preparations is by processing blood preparations using a leukocyte removing filter. Conventionally, blood preparations have been processed using a leukocyte removing filter in many cases at the bedside when blood transfusion is performed. In recent years, however, to improve quality control of leukocyte-free preparations and efficiency of leukocyte removal operations, it is more common to process the blood preparations in blood centers before storing the blood preparations.

A blood collection-separation set, typically consisting of two to four flexible bags, a tube connecting these bags, an anticoagulant, an erythrocyte preservation solution, a blood-collecting needle, and the like has been used for collecting blood from a donor, separating the blood into several blood components, and storing the blood components. A system in which a leukocyte removing filter is incorporated into such a blood collection-separation set has been widely used as an optimum system for the above-mentioned pre-storage leukocyte removal. Such a system is called a closed system or an integrated system and the like. Such a system is disclosed in JPA 1-320064, WO 92/20428, and the like.

Conventionally, a filter made from nonwoven fabric or porous filter elements packed in a hard container of polycarbonate or the like has been widely used as a leukocyte removing filter. However, because the container used in such a filter d, International Publication Number WO98/51799oes not have gas permeability, it has been difficult to use a vapor sterilization method, which is a widely accepted sterilization method in blood collection-separation sets. In a closed system, leukocytes are first removed from the whole blood preparation after collecting the blood. Then, after the leukocyte removing filter is separated, the leukocyte-free blood is centrifuged for separation into various components. In another type of closed system, the whole blood is first centrifuged to be divided into various components, and then the leukocytes are removed. In the latter system, the leukocyte removing filter is also centrifuged together with the blood collection-separation set. In this instance, a hard container may damage bags and tubes, or the container itself may not withstand the stress and may collapse during centrifugation.

To solve this problem, flexible leukocyte removing filters, in which the container is made of the same or a similar material having superior flexibility and high vapor permeability as used for the bags of the blood collection-separation set, have been developed.

These filters are broadly classified into the type in which the filter elements are welded to a sheet-like flexible frame, which is then welded to a housing material (EP 0 526 678, JPA11-216179) and the type in which the flexible container is directly welded to the filter elements (JPA 7-267871, WO 95/17236).

The former type may be hereinafter called the frame welding type and the latter may be called the container welding type.

When processing blood in these types of leukocyte removing filters, the bag containing a blood preparation to be processed, connected to the blood inlet port of the filter via a tube, is placed at a height 20-100 cm higher than the filter to allow the blood preparation to pass through the filter by action of gravity. After filtration, the blood preparation is stored in a collection bag connected to the blood outlet port of the filter via a tube. During filtration, a pressure loss is caused due to the resistance of the filter element, whereby the pressure in the space on the inlet side of the filter is maintained positive. In the case of the filter attached to a flexible container, the flexibility of the container itself makes the container swell like a balloon due to the positive pressure, thereby pressing the filter element against the outlet port side container. Specifically, a force acting to separate the filter element from the container or the sheet-like frame is always applied to the joining sections of these parts.

In the case of centrifuging the leukocyte removing filter together with the blood collection-separation set, a force acting to separate the filter element from the sheet-like frame or the flexible container may also be applied to the joining sections of these parts. As an example, the centrifuge operation using a one-liter-cylindrical centrifuge cup, which is typically employed in the United States and other countries, will be described. A hypothetical system consisting of a blood bag made of soft polyvinyl chloride containing 570 ml of a whole blood preparation treated for anti-coagulation, a blood processing filter, a bag made of soft polyvinyl chloride containing about 100 ml of an erythrocyte preservation solution, an empty bag for transferring platelet-rich plasma after centrifugation, and an empty bag to store the blood after processing with the blood processing filter arranged in this centrifuge cup in that order to be centrifuged will be discussed. Tubes made of soft polyvinyl chloride to connect the bags to the filter are appropriately arranged between the bags and the filter. The bags and the filter are pressed to the bottom of the centrifuge cup due to the centrifugal force. The bag containing the whole blood preparation and the bag containing an erythrocyte preservation solution are deformed causing them to swell due to the centrifugal force. As a result, the flexible blood processing filter placed between the two blood bags may be crushed by the blood bags or may be deformed into a configuration conforming to the blood bags. Although the mechanism differs from the above case in which the container swells like a balloon, as a result, the same force acting to separate the filter element from the sheet-like frame or the flexible container is applied.

The soft polyvinyl chloride and polyolefin, widely used as materials for containers or frames, exhibit only slight adhesion to the materials popularly used for filter elements such as polyester fibers and polyurethane porous materials. For these reasons, the joining parts have a problem of being easily separated by a comparatively small force. However, the above-mentioned prior art documents, including EP 0 526 678, Japanese Patent Application Laid-open Publication No.11-216179, Japanese Patent Application Laid-open Publication No. 7-267871, and WO 95/17236, or the like, disclosing flexible filters have neither realized this problem nor described the methods of overcoming the problem.

As a matter of fact, commercially available frame attachment type filters do not necessarily have sufficient resistance to the force acting to separate the joining parts of the filter element and the frame. These filters have a risk of invalidating filtration due to detachment of the filter element from the frame during use.

Although there are few commercially available container welding type filters, such filters also have a risk of container breakage or leaking due to the same reasons of separating the filter element from the container during use.

Beside the usual filter operation utilizing gravity, the filter may be compulsory primed with blood by pressing or squeezing the bag containing the blood preparation to be filtered by hand (hereinafter may be called "squeezing") or may be operated at a high speed by applying a high pressure using a pump. For these reasons, a filter with superior resistance to pressure and separation has been desired.

Furthermore, during the common filter operation utilizing gravity, a flexible container swells like a balloon due to the positive pressure applied to the blood inlet side of the filter as mentioned above. In this instance, the internal filter element bends by being pressed toward the outlet port side container. On the other hand, the space between the outlet port side container and the filter element tends to move toward the bag for storing the processed blood, which is located 50-100 cm lower than the filter by being caused to descend due to the weight of blood in the tube connected to the outlet port. A negative pressure is created by this action, whereby the outlet port side flexible container tends to be caused to adhere to the filter element. Specifically, the filter element is known to closely adhere to the outlet port side container by the double forces, whereby blood flow is obstructed.

As a means for solving this problem, a method of inserting a soft polyvinyl chloride tube called as "a connecting rod" between the filter element and outlet port side container to prevent adherence (EP 0526 678), a method of inserting a screen made of nit fiber (WO 95/17236), a method of preventing adhesion by providing irregularities with a depth of 0.2-2 mm on the internal surface of the soft container (Japanese Patent Application Laid-open Publication No. 11-216179), and other methods have been proposed. However, as described in Japanese Patent Application Laid-open Publication No. 11-216179, the method of inserting a connecting rod or a screen has been considered to have a risk of inducing defective welding of the container if the other materials are inserted. Although the method disclosed in Japanese Patent Application Laid-open Publication No. 11-216179 has been proposed as a measure for solving the problem in the method of inserting a connecting rod or a screen, the solution of the problem was limited to the case in which a soft container is welded with a flexible sheet-like filter. Specifically, although irregularities on the internal surface of the container do not cause a problem for welding the container material with the sheet frame material, the irregularities on the internal surface of the container may cause defective welding when the container material is directly welded with the filter element. Thus, the method was not necessarily satisfactory.

DISCLOSURE OF THE INVENTION

An object of the present invention is to provide a flexible blood processing filter, in which the blood flow may not be affected when the filter element is pressed to the outlet port side container due to the positive pressure on the inlet port side or the outlet port side container is caused to adhere to the filter element due to the negative pressure on the outlet port side during filtration operation. Another object of the present invention is to provide a flexible blood processing filter with superior pressure resistance, separation resistance, and sufficient strength against the pressure during filtration or the stress during centrifugation. Still another object of the present invention is to provide a flexible blood processing filter which can resist a higher pressure generated by a squeezing operation or rapid filtration using a pump, without causing problems such as leaking, fracture, and separation.

As a result of extensive studies to achieve the above objects, the present inventors have found that if a filter element having specific characteristics and a specific thickness is disposed in the most downstream location in contact with the outlet port side container, the blood flow is not obstructed by a blood processing filter having a flexible container. This finding has led to the completion of the present invention. The present inventors have further found that if a filter element having specific characteristics and a specific thickness is disposed in the most downstream location in contact with the outlet port side container, not only the blood flow is not obstructed in either the frame welding type filter or the container welding type filter, but also the filter exhibits remarkably excellent performance in pressure resistance and separation resistance. More surprisingly, the inventors of the present invention have found that when such a filter element is used, an excellent blood flow can be maintained even after there is almost no gravity effect on the inlet port side, by which it is possible to reduce the recovery time during the period close to the end of filtration operation. These findings have also led to the completion of the present invention.

As a result of further investigation on the pressure resistance and separation resistance, the inventors of the present invention have found that if a composite material layer with a specified thickness, in which part of the filter element is embedded in the materials of the sheet-like frame or the container in the joining area of the flexible sheet-like frame or flexible container and filter element, is provided, the filter exhibits excellent separation resistance and fracture resistance. The finding has also led to the completion of the present invention.

Specifically, the present invention provides a blood processing filter comprising a flexible container, which has an inlet port and an outlet port, and a sheet-like filter element for removing undesirable components from blood, wherein the blood inlet port is separated from the outlet port by the filter element, the sheet-like filter element comprises a first filter element for removing aggregate from blood, a second filter element arranged downstream of the first filter element to remove leukocytes, and a third filter element arranged between the second filter element and the outlet port side container to prevent the filter element from adhering to the outlet port side container and obstructing the flow of blood, wherein the third filter element has a gas permeability per 1 cm thickness of 3-40 cc/cm$^2$/sec and a thickness of 0.04-0.25 cm (such a filter is hereinafter referred to from time to time as three-element filter).

The three-element filter preferably has a seal zone formed by integrating the section near the periphery of the sheet-like filter element with the flexible container over its entire circumference. More preferably, the three-element filter has a first seal zone formed by integrating the section near the periphery of the sheet-like filter element with the flexible container over its entire circumference, a second seal zone formed by integrating the inlet side flexible container and the outlet side flexible container over the entire outside circumference of the first seal zone, and an unsealed zone disposed between the first seal zone and the second seal zone. Such a blood processing filter is hereinafter referred to as a "container welding type three-element filter" from time to time. In addition, irrespective of the presence or absence of the second seal zone, a seal zone formed by integrating the section near the periphery of the sheet-like filter element with the flexible container over its entire circumference is hereinafter referred to as "first seal zone" from time to time.

The present invention further provides a three-element blood processing filter comprising at least one flexible sheet-like frame between the flexible container and the sheet-like filter element, wherein the inlet port is separated from the outlet port by the filter element and the at least one sheet-like frame.

The blood processing filter preferably has a first seal zone formed by joining the entire circumference of the section near the periphery of the sheet-like filter element and at least one sheet-like frame, and a second seal zone formed by integrating the inlet side flexible container, at least one sheet-like frame, and the outlet side flexible container over the entire outside circumference of the first seal zone. Such a blood processing filter is hereinafter referred to as a "frame welding type three-element filter" from time to time.

In a further aspect, the present invention provides a blood processing filter comprising a flexible container, which has an inlet port and an outlet port, and a sheet-like filter element for removing undesirable components from blood, wherein the blood inlet port is separated from the outlet port by the filter element, a seal zone is formed by integrating the section near the periphery of the sheet-like filter-element with the flexible container over its entire circumference, the cross-section of the seal zone comprises at least five layers from the blood inlet side to the outlet side, that is, a layer consisting only of the inlet side flexible container material, an inlet port side composite material layer wherein the inlet side flexible container material is mixed with the filter element material, a layer consisting only of the filter element material, an outlet port side composite material layer wherein the outlet port side flexible container material is mixed with the filter element material, and a layer consisting only of the outlet port side flexible container material wherein both the inlet port side composite material layer and the outlet port side composite material layer have a thickness between 0.15 mm and 0.4 mm. Such a blood processing filter is hereinafter referred to as a "container welding type composite layer filter" from time to time.

The present invention further provides a blood processing filter having a composite material layer comprising at least one flexible sheet-like frame between the inlet port side flexible container and/or the outlet port side flexible container and the sheet-like filter element wherein the blood inlet port is separated from the outlet port by the filter element and at least one sheet-like frame, and the blood processing filter has a first seal zone formed by joining the entire circumference of the section near the periphery of the sheet-like filter element and at least one sheet-like frame, and a second seal zone formed by integrating the inlet side flexible container, the outlet side flexible container, and at least one sheet-like frame over the entire outside circumference of the first seal zone wherein the cross-section of the first seal zone has at least three layers, which are a layer consisting only of the sheet-like frame material, a composite material layer wherein the sheet-like frame material is mixed with the filter element material, and a layer consisting only of the filter element material, and the composite material layer has a thickness between 0.15 mm and 0.4 mm. Such a blood processing filter is hereinafter referred to as a "frame welding type composite layer filter" from time to time.

In the above-mentioned container welding type composite layer filter and the frame welding type composite layer filter, the sheet-like filter element preferably comprises a first filter element for removing aggregate from blood, a second filter element arranged downstream of the first filter element to remove leukocytes, and a third filter element arranged between the second filter element and the outlet port side container, wherein the third filter element has a thickness of 0.04-0.25 cm and a gas permeability of 3-40 $cc/cm^2/sec$ per thickness of 1 cm.

The container welding type three-element filter and container welding type composite layer filter are collectively referred to as container welding type blood processing filters from time to time. Similarly, the frame welding type three-element filter and frame welding type composite layer filter are collectively referred to as a frame welding type blood processing filter from time to time. In addition, the container welding type composite layer filter and frame welding type composite layer filter are collectively referred to as a composite layer filter from time to time.

BEST MODE FOR CARRYING OUT THE INVENTION

Figure 1:
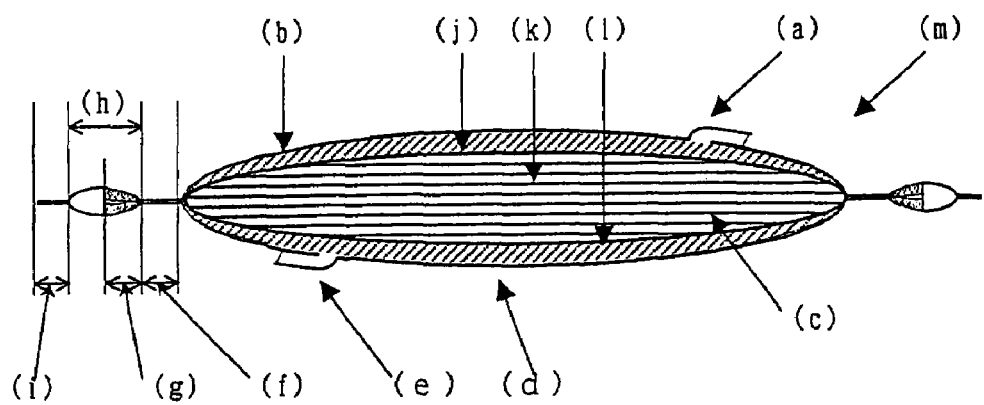
FIG. 1 is a schematic sectional view of a container welding type blood processing filter of the present invention.

The present invention will be described in more detail below.

The entire shape of the blood processing filter of the present invention may be rectangular, lozenge-shaped, disk-like, or oval. A rectangular or lozenge-shaped filter is preferable for decreasing loss of materials when manufacturing the filters. In this specification, a square configuration is included in the rectangular configuration.

The flexible container used in the present invention is preferably formed from a flexible sheet-like or a cylindrical formed object of a synthetic resin, preferably a thermoplastic resin.

The inlet port and outlet port for blood maybe integrally formed with the flexible container when the container is formed by injection molding or the like. Alternatively, holes or slits maybe provided in an extrusion-molded sheet-like film or cylindrical film, and then, the holes or slits may be liquid-tightly and communicatingly joined with parts for the inlet port and outlet port, made by injection molding or extrusion molding, by a known method such as a method of using an adhesive, heat sealing, or high frequency welding. The latter method is more preferable because of the rare chance of the container being deformed during sterilization using vapor and ease of manufacturing.

When the filter has a sheet-like frame, tubular sections that can function as an inlet port and an outlet port for blood may be inserted and bonded between the sheet-like or cylindrical film and the sheet-like frame.

When the parts for the inlet port and outlet port including tubular sections are liquid-tightly attached to the sheet-like or cylindrical film, the material of the parts for the inlet port and outlet port may be either the same as or different from the material for the sheet-like or cylindrical film. When different materials are used, there are no specific limitations to the types of the materials in as much as the inlet and outlet ports can be liquid-tightly joined with the sheet-like or cylindrical film and can be handled without a problem. However, when these parts are connected using a means suitable for mass production such as heat sealing or high frequency welding, a material having thermal and electrical properties similar to the sheet-like or cylindrical film is preferable.

When two materials, both having a comparatively high dielectric constant such as soft polyvinyl chloride, are used, high frequency welding can suitably join these materials. When two materials, both having a comparatively low dielectric constant and comparatively low melting point such as polyolefin, are used, heat sealing can suitably join these materials.

The flexible container and frame-shaped sheet of the present invention are preferably made of materials having thermal and electrical properties similar to the material for the filter element. For example, thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate, and the like can be given as preferable materials. Of these, preferable materials are thermoplastic elastomers such as soft polyvinyl chloride, polyurethane, ethylene-vinyl acetate copolymer, polyolefin, and mixtures the thermoplastic elastomers containing these mixtures as a major component, with particularly preferable materials being soft polyvinyl chloride and polyolefin.

The sheet-like filter elements used for the three-element filter of the present invention comprises a first filter element for removing aggregate from blood, a second filter element arranged downstream of the first filter element to remove leukocytes, and a third filter element arranged between the second filter element and the outlet port side container. The third filter element has a gas permeability of 3-40 cc/cm$^2$/sec per thickness of 1 cm and a thickness of 0.04-0.25 cm. The sheet-like filter element in a composite layer filter need not necessarily comprise the first, second, and third filter elements, but preferably comprises the first and third filter elements from the viewpoint of ease of forming the composite material layer The gas permeability herein used indicates the amount of permeating air (cc/cm$^2$/second) measured by the test method described in JIS L-1096, 6.27.1 A-method (1992 edition) and the gas permeability per thickness of 1 cm indicates the value obtained by multiplying the gas permeability by the thickness (cm) of the third filter element.

The thickness herein used indicates the value determined by measuring the thickness at 1.5 N using a dial gauge with a measuring piece having a diameter of 10 mm according to the method defined in JIS B7503 (1992 edition). When the third filter element is made of two or more materials, such as several sheets of nonwoven fabric, woven fabric, and the like, for example, the gas permeability and thickness for each sheet are measured and then the gas permeability per 1 cm thickness is determined. The third filter element of the present invention must have the gas permeability within the range of 3-40 cc cm$^2$/sec, with a total thickness being 0.04-0.25 cm. For example, a third filter element containing a filter element having a gas permeability of less than 3 cm$^2$/sec or a filter element having a gas permeability of more than 40 cm$^2$/sec inserted between the filter elements having a gas permeability of 3-40 cc cm$^2$/sec is included in the scope of the present invention.

The gas permeability for one sheet of the third filter element may not be easily determined by a standard method according to the above test when the fiber diameter or the pore diameter of the third filter element is too large or the thickness of one sheet is too thin. In this instance, after determining the gas permeability by laminating several sheets or by masking a part of the area of the test specimen for which the gas permeability is measured, the value for one sheet or for one unit area can be determined by converting the measured value.

The third filter element allows the blood going to the outlet port after passing through the second filter element to flow in the third filter element in the direction perpendicular to the thickness of the filter element, even in the case in which the filter element is caused to adhere to the outlet port side container due to the positive pressure on the filter inlet side and the negative pressure on the filter outlet side, whereby the time required for filtration and recovery can be shortened.

In the case in which the gas permeability per 1 cm thickness is less than 3 cc/cm$^2$/sec, the above blood flow in the perpendicular direction after passing through the second filter element cannot be sufficiently achieved, resulting in retardation of filtration and, in particular, recovery. If the gas permeability per 1 cm thickness is more than 40 cc/cm$^2$/sec, the pressure resistance and separation resistance may be insufficient.

A more preferable range for the gas permeability per 1 cm thickness is 3.5-10 cc/cm$^2$/sec, with an optimum range being 4-9 cc/cm$^2$/sec.

If the thickness of the third filter element is less than 0.04 cm, the blood flow in the perpendicular direction becomes insufficient, resulting in retardation of filtration time. When the thickness of the third filter element is more than 0.25 cm, on the other hand, the effect of decreasing the filtration time and recovery time cannot be obtained any more. The third filter element increases the resistance to the blood flow, which not only gives rise to retardation of the filtration time and recovery time on the contrary, but also increases loss of the blood preparations.

A more preferable thickness of the third filter element is 0.05-0.20 cm, with the range of 0.06-0.15 cm being ideal.

Known filter media, such as porous fiber materials including nonwoven fabric, woven fabric, and mesh, as well as porous materials having three-dimensional braided continuous pores can be used as the filter element in the present invention. The materials for such filter media include polypropylene, polyethylene, styrene-isobutylene-styrene copolymer, polyurethane, polyester, and the like.

Usually, filter media with different fiber diameter and pore diameter are used for the first filter element and the second filter element. For example, a filter material with a fiber diameter between several μm to several tens of μm is arranged in the inlet side as a first filter element for removing aggregate, a filter material with a fiber diameter of 0.3-3.0 μm is arranged next as a second filter element for removing leukocytes, and a third filter is laminated downstream of the second filter element.

Each of the first, second, and third filter elements may be formed further from two or more different filter elements. In this instance, the first and second filter elements are preferably arranged so that the fiber diameter increases stepwise or continuously from the section of the second filter element with the smallest fiber diameter toward the inlet port and the outlet port.

In the same manner, when porous materials having three-dimensional braided continuous pores are used as the first and second filter elements, these filter elements are preferably arranged so that the pore diameter increases stepwise or continuously from the section of the second filter element with the smallest pore diameter toward the inlet port and the outlet port.

In the same manner, the third filter element is preferably arranged so that the fluid permeability per 1 cm thickness increases either stepwise or continuously from the section in contact with the second filter element toward the section in contact with the outlet port side container.

The first seal zone in the container welding type filter and the first seal zone in the frame welding type filter of the present invention (hereinafter may be referred to collectively as "first seal zone") can be formed by joining the flexible container or the frame-like sheet with the section near the periphery of the filter element by internal welding using a high frequency welding method or a supersonic wave welding method or by external welding with heat. The high frequency welding method is preferably used when the container or the frame-like sheet and the filter element are made from materials with a comparatively high dielectric constant, and the heat sealing is preferably used when either one material has a low dielectric constant or both materials have a low melting point.

The first seal zone may be formed either in the outermost periphery of the filter element or in a point slightly inside the outermost periphery, for instance, a point several mm inside the periphery. The latter case is more preferable because the several mm margin of the filter element, which is left unsealed outside the first seal zone, ensures safe and sure sealing.

It is unnecessary for the entire filter elements to be integral with the flexible container or the sheet-like frame in the first seal zone. In the three filter elements of the present invention, it is desirable that at least the second filter element, a part of the first filter element contacting the second filter element, and a part of the third filter element contacting the second filter element be integral. It is more preferable that all the filter elements be integral. The first filter element and third filter element, which are to be integrally formed, have a thickness of preferably 50-1,000%, more preferably 70-500%, and still more preferably 100-250% of the thickness of the container or the sheet-like frame to be integrated. Although the thickness of the container or the sheet-like frame should be defined as the thickness for the section corresponding to the first seal zone before joining, it is possible to replace such a thickness corresponding to the first seal zone with the thickness of the container material or the sheet-like frame material adjacent to, but at inner side from, the seal zone after joining.

In addition, in the container welding type composite layer filter of the present invention, the cross-section of the first seal zone comprises at least five layers from the blood inlet side to the outlet side, that is, a layer consisting only of the inlet port side container material, an inlet side composite material layer wherein the inlet port side container material is mixed with the filter element material, a layer consisting only of the filter element material, an outlet side composite material layer wherein the outlet port side container material is mixed with the filter element material, and a layer consisting only of the outlet port side container material or the sheet-like frame. Both the inlet side composite material layer and the outlet side composite material layer have a thickness of 0.15-0.4 mm.

The frame welding type composite layer filter has a cross-section of the first seal zone comprising at least 3 layers, that is, a layer consisting only of the sheet-like frame material, a composite material layer wherein the sheet-like frame material is mixed with the filter element material, and a layer consisting only of the filter element material. The composite material layer has a thickness of 0.15-0.4 mm. When a sheet-like frame is joined with a filter element, the sheet-like frame may be located either on the upstream side or on the downstream side of the filter element. In the former case, at least three layers are observed in the cross-section of the seal zone, which are, from the blood inlet side to the outlet side; a layer consisting only of the sheet-like frame material, a composite material layer wherein the sheet-like frame material is mixed with the filter element material, and a layer consisting only of the filter element material. In the latter case, at least three layers are observed, which are, from the blood inlet side to the outlet side, a layer consisting only of the filter element material, a composite material layer wherein the sheet-like frame material is mixed with the filter element material, and a layer consisting only of the sheet-like frame material.

It is possible to form a first seal zone consisting of five layers, wherein the filter elements are sandwiched by two sheet-like frames. The five layers are, from the blood inlet side to the outlet side, a layer consisting only of the inlet side sheet-like frame material, a composite material layer wherein the inlet side sheet-like frame material is mixed with the filter element material, a layer consisting only of the filter element material, a composite material layer wherein the outlet side sheet-like frame material is mixed with the filter element material, and a layer consisting only of the outlet side sheet-like frame material.

In this case, either the sheet-like frame on the inlet side or the sheet-like frame on the outlet side must be integrated with the flexible material on both the inlet side and the outlet side, thereby forming the second seal zone. Since the main stress is applied to the sheet-like frame side integrated with the container, the thickness of the composite material containing the sheet-like frame forming the second seal zone and the filter element as major components must have a thickness of 0.15-0.4 mm. This thickness requirement does not necessarily apply to the composite material containing the sheet-like frame not forming the second seal zone and the filter element as major components.

The composite material layer of the present invention is preferably a layer made from of the material of the container or sheet-like frame invading voids of the filter element material which becomes molten with relatively difficulty, resulting in a layer in which the former material embeds the fibrous or porous material of the filter element therein.

The thickness of the composite material layer must be between 0.15 to 0.4 mm. If the thickness of the composite material layer is smaller than 0.15 mm, sufficient separation resistance and fracture resistance cannot be obtained.

As mentioned above, soft polyvinyl chloride, polyolefin, and the like widely used as materials for containers or frames, exhibit only slight adhesion to the materials popularly used for filter elements such as polyester fibers and polyurethane porous materials.

A process for fabricating the composite material layer and the feature of such a process will now be described for the case of forming a composite material layer on the inlet port side in container welding type filter from the container material of soft polyvinyl chloride and the first filter element made of polyester fiber using high frequency welding technology. To join the outlet port side container material with the filter element and inlet port side container material by means of high frequency welding, these materials are laminated, put into a metal mold for high frequency welding, and pressed at a prescribed pressure. Then, a high frequency current is applied. The soft polyvinyl chloride heated by the high frequency wave becomes softened and molten and invades voids of fibers in the first filter element by the pressure from the metal mold. In this instance, the first filter element is not sufficiently heated to a temperature to cause the fibers to become molten. In addition, since the fibers have a melting point higher than the container material, the fibers are left as is without becoming molten. The container material invades the fiber voids, resulting in a composite material layer, in which the fibers are embedded by the material of the container. On the other hand, an inner filter element, for example, the second filter element in the present invention, tends to become heated from around the center in terms of the thickness of the entire filter element. As a result, the filter element is heated by the high frequency wave to the melting point earlier than the time when the container material invades from the inlet side and becomes molten to the extent that the molten material reaches the composite material. As a result of formation of the composite material layer also on the outlet side in the same manner, a first seal zone consisting of five layers is ultimately formed.

The thickness of the composite material layer is determined by the balance of the invasion speed of the container material and the melting speed of the filter element. However, since the invasion speed of the container material is affected by the different fiber diameters and pore sizes of the filter element, the thickness of the composite material layer is determined as a result of extremely complicated phenomena involving various factors other than the high frequency welding conditions when two or more filter elements with different fiber diameters and pore sizes are used. Therefore, it is preferable to determine the conditions for forming a composite material layer with a desired thickness by previous experiments.

The first seal zone can be formed from a sheet-like frame material and a filter element material in the same manner also in the case of the frame welding type filter.

In the composite material layer formed according to the above-described process, when the container material or the sheet-like frame material encompassing fibers do no have adhesion with the fibers, it is important for the filter element to be sufficiently engaged with the container material or the sheet-like frame material to resist the force acting to separate the container or the sheet-like frame from the filter element. Such engaging strength is thought to have a certain correlation with the thickness of the composite material layer. Therefore, at the beginning of examination of the present invention, it was anticipated that the thicker the composite material layer, the stronger the engaging strength. Unexpectedly, however, it was found that some composite material layers with a thickness exceeding 0.4 mm have inferior pressure resistance in some cases, that is, fluctuated pressure resistance and separation resistance. The thickness of the composite material layer therefore must be 0.4 mm or less.

A more preferable thickness of the composite material layer is 0.18-0.35 mm, with the range of 0.23-0.33 mm being ideal. In addition, the thickness of the outlet port side composite material layer is preferably as close as the thickness of the inlet port side composite material layer. Specifically, the thickness difference is preferably within 0.1 mm, and more preferably within 0.05 mm.

The invasion speed of the container material may be larger than the melting speed of the filter element depending on the selection of the construction of the filter element and high frequency welding conditions. In such a case, the entire container material may invade the first filter element before the second filter element melts and expands. The fiber diameter and pore size of the second filter element for removing leukocytes are usually smaller than those of the first filter element by far. The material for the container cannot easily invade such fibers and pores even in the molten state. As a result, layers consisting only of the container material, which are considered to have been formed from the invaded container material, may be observed between the first filter element and the second filter element. In this instance, the container material and the second filter element, which are not inherently adhesive, come into contact along a surface , resulting in decreased pressure resistance and separation resistance.

Therefore, fibers of the first filter element, of which one half the amount is embedded in the container material and the other half is molten with the second filter element and embedded therein, are preferably present in the interface of the composite material layer and the layer consisting only of the filter element. In such an instance, a boundary line between the composite material layer and the layer consisting only of the filter element exhibits a complicated microstructure (hereinafter may be referred to as "anchor structure") in the cross-section of the first seal zone. Although an example of the anchor structure in the first filter element formed from fibers has been described above, such an anchor structure may be formed in the second filter element, the third filter element, or the filter element formed from porous material having three-dimensional braided continuous pores.

The thickness of the composite material layer can be determined by various methods such as a method of previously specifying a point in the first seal zone at which the layers are most likely to separate and cutting the section including that point to inspect the reflection electronic image using a scanning electron microscope, a method of employing both the inspection using a scanning electron microscope together with EDX analysis (energy dispersive X-ray analysis), a method of applying an etching treatment, for example, by coating a solvent which selectively dissolves one of the materials forming the composite material layer, followed by inspection using a scanning electron microscope or a laser microscope, and the like. The method of observing the reflection electronic image using a scanning electron microscope is suitable for inspecting the anchor structure. A simple method of specifying the easily separated point in the container welding type filter is closing the blood outlet port with a clamp and feeding pressurized air from the blood inlet port until the container fractures (this method may be hereinafter referred to as "burst test").

The burst test for the frame welding type filter is carried out after forming a structure similar to the container welding type filter by joining the sheet-like frame with a sheet-like material having a configuration the same as or similar to the frame. Alternatively, a method of measuring the separation strength at each section of the first seal zone using an Instron-type all-purpose tensile compression tester may be employed for the burst test for the frame welding type filter. The first seal zone usually has a width of several mm. If the thickness of the composite material layer differs within this range of width, the thickness at several points wherein the anchor structure is observed is measured and the average of the measured values is employed. When it is difficult to specify the anchor structure, the thickness of the point having the maximum thickness is regarded as the thickness of the composite material layer.

The width of the first seal zone is preferably 1-6 mm, more preferably 2-5 mm, and still more preferably 3-4 mm. If less than 1 mm, the joined part becomes like a line, which has a risk of failing to exhibit sufficient sealing performance when subjected to high-pressure vapor sterilization or roughly handled. The first seal zone with a width exceeding 6 mm, which tends to become hardened by high frequency welding, heat sealing, or the like, becomes excessively wide, whereby part of the characteristics as a flexible container may be lost, that is, not preferable.

The sheet-like frame used for the frame welding type blood processing filter of the present invention indicates a frame-shaped material prepared by deleting the part corresponding to the effective filtering section inside the first seal zone from a flexible sheet-like formed material by means of cutting or punching. The sheet-like frame formed by injection molding into a frame-shaped product may also be included. The term "frame-shaped" herein used is not limited to a shape with a rectangular contour, but includes a shape produced from a lozenge-shaped object, a circular object, or oval object by removing the inner portion and leaving the periphery, according to the shape of the flexible container or the effective filtration part.

The sheet-like frame must be provided on either the blood inlet side or outlet side, but may be provided on both the inlet and outlet sides. The portion near the inner periphery of the sheet-like frame must be integrated with the portion near the outer periphery of the filter element to form the first seal zone. In addition, the outer periphery of the frame must be integrated with the inlet port side container and the outlet port side container to form the second seal zone. However, when the frame is provided on both the inlet side and outlet side, it is only necessary for the frame to be integrated with either the inlet port side container or the outlet port side container to form the second seal zone, thereby isolating the inlet port from the outlet port by the filter element and the sheet-like frame. It is thus unnecessary for the frame to be integrated with both the inlet port side container and the outlet port side container to form the second seal zone. The filter element is indirectly joined with the container via the sheet-like frame, whereby an upstream chamber surrounded by the uppermost part of the filter element, the inlet port side container, and the sheet-like frame, to which the blood inlet port is connected, and a downstream chamber surrounded by the lowermost part of the filter element, the outlet port side container, and the sheet-like frame, to which the blood outlet port is connected are formed. In this manner, a filter with the blood inlet port being separated from the outlet port by the filter element and the sheet-like frame is formed.

A known method such as high frequency welding, internal welding by supersonic wave welding, external welding by heat sealing, adhesion using a solvent, or the like can be used for forming a second seal zone. The high frequency welding is preferably used when the flexible container is made from a material with a comparatively high dielectric constant, and the heat sealing is preferably used when the material has a low dielectric constant and a low melting point.

The width of the second seal zone is preferably 1-10 mm, and more preferably 2-5 mm. If less than 1 mm, sealing performance may not be relied upon. A width of 10 mm or less is desirable because an unnecessarily wide weld increases the amount of material used.

A second seal zone, formed by integrating the inlet side flexible container material with the outlet side flexible container material over their entire circumference, may be provided outside the seal zone in the container welding type filter of the present invention. In this case, for the sake of distinguishing from the second seal zone, the seal zone formed by integrating the container material with the filter material may be called a first seal zone of the container welding type filter. Since the second seal zone can avoid the risk of exposing the medical workers to the danger of infection or prevent blood preparations from being contaminated with miscellaneous bacteria in the case the first seal zone is broken to leak due to operational mistakes or rough handling, stress of centrifugal operation, or as such during filtering operation, it is preferable also for the container welding type filter to be provided with a second seal zone.

Still more preferably, the container welding type filter is provided with an unsealed zone between the first seal zone and the second seal zone. In this instance, the width of the unsealed zone is preferably 1-30 mm. The unsealed zone makes it easy to detect leaking occurring in the first seal zone.

The flexible container of the present invention may be formed either from a film-like sheet or a cylindrical sheet. When the blood processing filter is formed from a film-like sheet, a filter element may be sandwiched between two film sheets. It is also possible to fold a film sheet and place the filter element in the folded film sheet.

When a first seal zone in the container welding type filter is formed from a folded film sheet and a filter element sandwiched in the folded film sheet, it is unnecessary to form the second seal zone over the entire circumference of the filter. The above object can be achieved by sealing only the open three sides. This feature is also within the scope of the present invention. When the first seal zone is formed in the container welding type filter by placing the filter element inside a cylindrical film, it is unnecessary to form the second seal zone over the entire circumference of the filter, but the above object can be achieved by sealing only the open two sides. This feature is also within the scope of the present invention.

One embodiment of the blood processing filter of the present invention is shown in FIG. 1, which should not be construed as limiting the present invention.

FIG. 1 is a schematic sectional view of a container welding type blood processing filter of the present invention. In a blood processing filter (m) comprising an inlet side flexible container (b) made from a sheet of resin equipped with a blood inlet port (a), an outlet side flexible container (d) made from a sheet of resin equipped with a blood outlet port (e), and a filter element (c) for removing undesirable components from blood, wherein the blood inlet port (a) and outlet port (e) are separated by the filter element (c), the filter element (c) has a first seal zone (f), which is disposed between the inlet side flexible container and the outlet side flexible container, integrated with the flexible container with the section near the periphery being welded with the flexible container over its entire circumference, and, outside the first seal zone, a second seal zone (i), integrated by welding the inlet side flexible container and outlet side flexible container. The first seal zone (f) is formed slightly inside the outermost periphery of the filter element (c). There is a filter element (g) left unsealed in an unsealed zone (h) at the outside of the first seal zone (f). The filter element (c) consists of a first filter element (j), a second filter element (k) and a third filter element (l).

Figure 2:
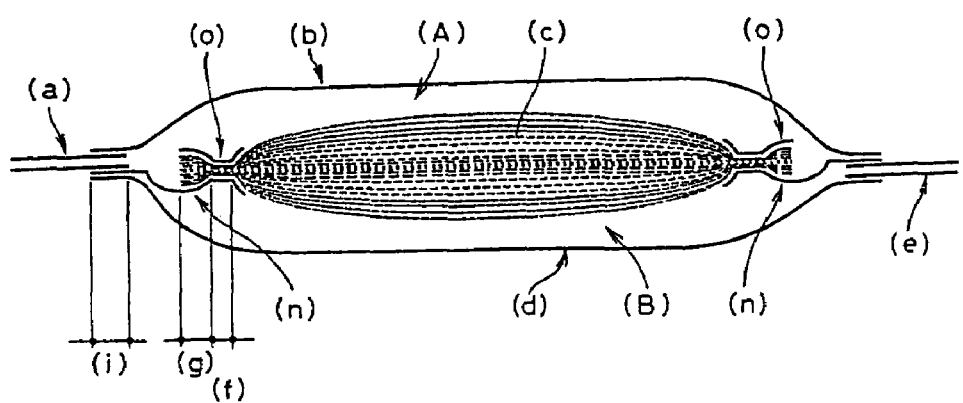
FIG. 2 is a schematic sectional view of the frame welding type blood processing filter of the present invention.

FIG. 2 is a schematic sectional view of a frame attachment type blood processing filter. A blood processing filter having a sheet-like frame disposed on both the inlet side and the outlet side, with only the outlet side sheet-like frame being integrated with the container in the second seal zone, is shown in FIG. 2. In FIG. 2, the same parts as those shown in FIG. 1 are indicated by the same symbols.

In the blood processing filter comprising a blood inlet port (a), the blood outlet port (e), an inlet side flexible container (b), an outlet side flexible container (d), a sheet-like filter element (c) for removing undesirable components from blood, an inlet side flexible sheet-like frame (o) disposed between the inlet side flexible container (b) and the sheet-like filter element (c), and an outlet side flexible sheet-like frame (n) disposed between the outlet side flexible container (d) and the sheet-like filter element (c), wherein the blood inlet port (a) and the outlet port (e) are separated by the filter element (c) and the outlet side flexible sheet-like frame (n), a first seal zone (f) is formed by joining the entire circumference of the section near the periphery of the sheet-like filter element and the two sheet-like frames, and a second seal zone (i) is formed by integrating the inlet side flexible container, the outlet side sheet-like frame, and the outlet side flexible container over the entire outside circumference of the first seal zone. The first seal zone (f) is formed slightly inside the outermost periphery of the filter element (c). Outside the first seal zone (f), there is a filter element (g) left unsealed. In the above configuration, an upstream chamber (A) encircled by the uppermost part of the filter element (c), the inlet side container (b), and the outlet side sheet-like frame (n), to which the blood inlet port (a) is connected, and a downstream chamber (B) encircled by the lowermost part of the filter element (c), the outlet side container (d), and the outlet side sheet-like frame (n), to which the blood outlet port (e) is connected, are formed whereby a blood processing filter with the blood inlet port and the outlet port being separated by the filter element and the outlet side sheet-like frame is formed.

Although the sheets in the first seal zone and the second seal zone are separately shown in FIG. 2 for ease of understanding, these elements may be integrally formed by welding in practice.

In addition, although the blood inlet and outlet ports are provided in the second seal zone in the embodiment shown in FIG. 2, the blood inlet and outlet ports for the frame welding type blood processing filter may be provided directly on the flexible container in the same manner as in FIG. 1.

Figure 3:
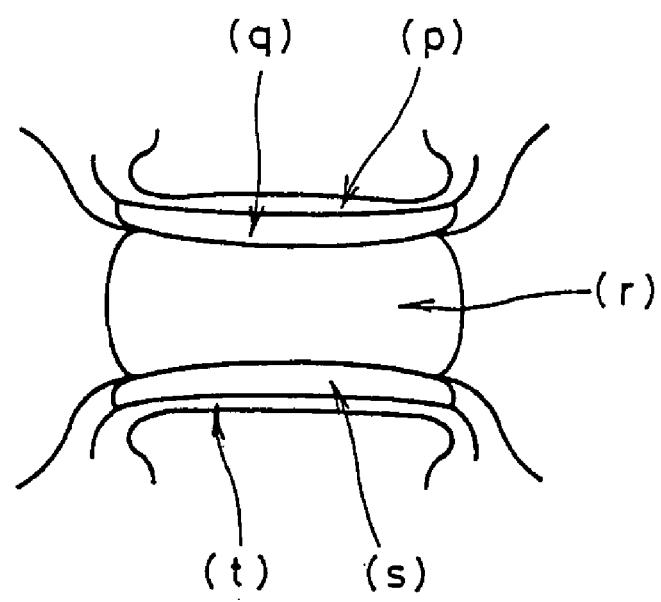
FIG. 3 is a schematic sectional view of the first seal region of the present invention.

FIG. 3 schematically shows the cross-section of a test specimen cut from the first seal zone of the blood processing filter shown in FIG. 1 or FIG. 2. The cross-section consists of the following five layers: a layer (p) made only of the material for the inlet side container or the sheet-like frame, an inlet side composite layer (q) made of a mixture of the material for the inlet side container or the sheet-like frame and the filter element material, a layer (r) made only of the filter element material, an outlet side composite layer (s) made of a mixture of the material for the outlet side container or the sheet-like frame and the filter element material, and a layer (t) made only of the material for the outlet side container or the sheet-like frame. These layers have the following thickness. The layer (p) made only of the material for the inlet side container or the sheet-like frame: 0.15 mm, the inlet side composite layer (q) made of a mixture of the material for the inlet side container or the sheet-like frame and the filter element material: 0.25 mm, the layer (r) made only of the filter element material: 0.9 mm, the outlet side composite layer (s) made of a mixture of the material for the outlet side container or the sheet-like frame and the filter element material: 0.23 mm, and the layer (t) made only of the material for the outlet side container or the sheet-like frame: 0.16 mm. The total thickness of the first seal zone is 1.69 mm.

EXAMPLES

The leukocyte removing filter of the present invention will now be described in detail by way of examples, which should not be construed as limiting the present invention.

(Measuring Method)

(1) Measurement of Recovery Time and Amount of Blood Loss

The blood processing filter of the present invention was disposed between a pre-processing blood reservoir and a post-processing blood recovery bag. An inlet side tube joined with the pre-processing blood reservoir was connected to the blood inlet port (a) of the blood processing filter and an outlet side tube joined with the post-processing blood recovery bag was connected to the blood outlet port (e) of the blood processing filter. A tube made of vinyl chloride, having an internal diameter of 3 mm, an external diameter of 4.2 mm, and a length of 50 cm was used for both tubes. A Y-shaped tube was joined around the center of both the inlet side tube and the outlet side tube. A bypass tube for joining these Y-shaped tubes was provided. In addition, a blood feeding tube for feeding the blood was joined to the pre-processing blood reservoir, thereby forming a system.

After closing the inlet side tube and bypass tube using clamps, 250 ml a high concentration solution of cow's erythrocyte, containing CPD (citrate phosphate dextrose) added thereto, was charged to the pre-processing blood reservoir from the blood feed tube. Thereafter, the blood feed tube was separated from the root and the opening left after the separation was sealed by heating.

The entire system was suspended and the post-processing blood recovery bag was allowed to stand on a balance. Then, the clamp closing the inlet side tube was released to open the tube, thereby starting filtration. Blood in the pre-processing blood reservoir flowed out by gravity, passed through the blood processing filter (m), and was collected in the post-processing blood recovery bag. During processing of blood, the inlet side of the blood processing filter (m) expanded like a balloon due to the action of gravity.

The pre-processing blood reservoir soon emptied. At this point in time, blood still remained in the blood processing filter (m) expended by the action of pressure. The remaining blood was collected in the post-processing blood recovery bag by the action of gravity. The period of time from the time when the pre-processing blood reservoir has emptied, through the time when the weight of the post-processing blood recovery bag has ceased to increase, until the time the blood remaining in the blood processing filter (m) has been collected is defined as recovery time.

After the completion of blood collection, a point between the Y-letter tube provided in the outlet side tube and the blood processing filter (m) was closed by a clamp. Then, the clamp that had closed the bypass tube was released while squeezing the post-processing blood recovery bag to push the air in the post-processing blood recovery bag up to the pre-processing blood reservoir. The bypass tube was closed again with the clamp when all the air in the post-processing blood recovery bag was evacuated. Then, the clamp between the Y-tube provided in the outlet side tube and the blood processing filter (m) was released and the system was allowed to stand, whereupon the air which had been pushed up into the pre-processing blood reservoir flowed in to initiate an air rinse. The amount of blood in the post-processing blood recovery bag increased by a volume equal to the amount of blood in the inlet side tube and the blood impregnated in the first filter element (j). The amount of blood remaining in the blood processing filter (m) and the tube after the air rinse was determined as the difference between the amount of blood before processing and the amount of blood after processing. This amount was defined as the amount of blood loss.

(2) Measurement of Container Strength

The blood processing filter was cut (length: about 20 mm) at two points across the first seal zone using a cutter. A test specimen was produced by cutting inside the first seal zone (an area about 30 mm inside from the effective filtering section) with the cutting direction being parallel to the first seal zone. Using a razor edge, irregularities on the cross-section of the first seal zone were shaved to make the surface smooth. The length of the first seal zone was measured by a three-point vernier caliper. The average was determined as the length of the first seal zone.

In this instance, the container and the filter element on the effective filtering section side in the container welding type blood processing filter were left attached without separating. For the system having a second seal zone, the container was separated in the unsealed zone to determine the strength only of the first seal zone. The containers on the inlet side and outlet side in the effective filtering section were secured using a gripper in the effective filtering section side at the point 10 mm from the first seal zone to draw the containers in the vertical direction at a speed of 10 mm/min, thereby applying a force acting to separate out the first seal zone.

Since there is no sheet-like frame material in an amount sufficient to be secured on the effective filtering section side by the gripper in the case of the frame welding type blood processing filter using a sheet-like frame, the same material was caused to adhere to the effective filtering section side of the sheet-like frame. The same experiment as above was carried out by grasping this material using the gripper.

In the above test, the maximum force required for the container to be completely separated was converted into force per unit length (1 mm) of the first seal zone (N/mm) using the length of the cut out first seal zone. The values were compared (hereinafter referred to as separation strength) The separation strength was measured at room temperature (23° C.) using a Universal Testing Machine RTC-1250 manufactured by Orientec Corp.

(3) Method of Measuring Thickness of Composite Material Layer

To inspect the cross-section of the first seal zone, a test specimen was cut out, using a cutter knife, from the effective filtering section through the second seal zone vertically across the first seal zone. Irregularities on the cross-section of the first seal zone were shaved with a razor edge to make the surface smooth. A photograph of the specimen prepared in this manner was taken using a scanning electron microscope to inspect the reflection electronic image. The thickness of the composite material layer was determined from the photograph. The thickness was measured at several points along the entire length of the first seal zone. The average of the anchor structural area or the value of the thickest part was used as the thickness of the composite material layer.

(4) Burst Test Method

A container welding type filter with the second seal zone cut out or without a second seal zone was prepared. The end of the filter element out side the first seal zone was exposed. After closing the blood outlet port with a clamp and joining the tube with the blood inlet port, the filter was immersed in water. Air under a pressure of 0.08 Mpa was fed from the tube to determine the period of time required for the first seal zone to be separated and for the air to begin to leak. The time thus determined was regarded as the container fracture time.

Since the filter element is brought to a condition as if the filter were clogged during the burst test of a frame welding type filter using a sheet-like frame, the burst test was carried out by causing the filter made of the same material as the sheet-like frame to adhere to the sheet-like frame on the inlet side of the filter element.

Example 1

A flexible sheet of polyvinyl chloride resin with a size 20 mm larger, both in the length and width, than the outer dimension of the second seal zone and a thickness of 0.037 cm was prepared. The sheet was provided with holes with a diameter equivalent to or larger than the internal diameter of the blood inlet and outlet ports in locations corresponding to the inlet and outlet ports when the sheet is caused to adhere to the container. Parts for the blood inlet and outlet ports having an internal diameter allowing the tube to be sealingly inserted therein were prepared from apolyvinyl chloride resin by injection molding. The parts for the blood inlet and outlet ports were attached to the holes of the polyvinyl chloride resin sheet by high frequency welding to obtain a flexible container (b) for the inlet port side equipped with the blood inlet port (a) and a flexible container (d) for the outlet port side equipped with the blood outlet port (e).

A laminate of the following sheets of nonwoven polyester fabric were used as the filter element (c). Four sheets of nonwoven fabric (1) with an average fiber diameter of 12 µm and a density of 30 g/m$^2$ was used as the first filter element (j). As the second filter element (k) a total 27 sheets of nonwoven fabric consisting of one sheet of nonwoven fabric (2) with an average fiber diameter of 1.7 µm and a density of 66 g/m$^2$, 25 sheets of nonwoven fabric (3) with an average fiber diameter of 1.2 µm and a density of 40 g/m$^2$, and one sheet of nonwoven fabric (2) were laminated in that order. As the third filter element (1), six sheets of nonwoven fabric, each having a thickness of 0.019 cm and a gas permeability per 1 cm thickness of 4.5 cc/cm$^2$/sec, were laminated to obtain a laminated sheet with a thickness of 0.114 cm. The three filter elements were laminated in that order. The laminated sheet of the three filter elements obtained as described above was cut into a rectangle of 91 mm×74 mm to be used as the filter element (c). The flexible containers (b, d) and the filter element (c) were layered in the order of the inlet port side flexible container (b), filter element (c), and outlet port side flexible container (d) and welded by high frequency welding to form the first seal zone with the dimension of a filtering section of 75 mm×58 mm and the width (f) of the first seal zone of 3 mm. In forming the first seal zone, the separation strength was previously tested to determine the high frequency welding conditions under which the separation strength becomes maximum when the above filter element (c) was used. A second seal zone was formed 3 mm outside the outermost circumference of the filter element by combining the inlet port side container and the outlet port side container by high frequency wielding to provide a width (i) of 4 mm for the second seal zone. The container material remaining outside the second seal zone was cut and removed.

The blood filter obtained in this manner was inspected according to the above-mentioned methods of measuring recovery time and the amount of blood loss to determine the recovery time and the amount of blood loss. In addition, the separation strength was determined according to the above-mentioned method of measuring the container strength. Each test was repeated five times to determine the average. The results are shown in Table 1.

Example 2

A filter was prepared in the same manner as in Example 1, except that as a third filter element three sheets of nonwoven fabric, each having a thickness of 0.019 cm and a gas permeability per 1 cm thickness of 4.5 cc/cm²/sec, were laminated to obtain a laminated sheet with a thickness of 0.057 cm. The recovery time, the amount of blood loss, and separation strength were determined. The results are shown in Table 1.

Example 3

A filter was prepared in the same manner as in Example 1, except that as a third filter element nine sheets of nonwoven fabric, each having a thickness of 0.019 cm and a gas permeability per 1 cm thickness of 4.5 cc/cm²/sec, were laminated to obtain a laminated sheet with a thickness of 0.171 cm. The recovery time, the amount of blood loss, and separation strength were determined. The results are shown in Table 1.

Example 4

A filter was prepared in the same manner as in Example 1, except that as a third filter element 12 sheets of nonwoven fabric, each having a thickness of 0.019 cm and a gas permeability per 1 cm thickness of 4.5 cc/cm²/sec, were laminated to obtain a laminated sheet with a thickness of 0.228 cm. The recovery time, the amount of blood loss, and separation strength were determined. The results are shown in Table 1.

Example 5

A filter was prepared in the same manner as in Example 1, except that as a third filter element four sheets of nonwoven fabric, each having a thickness of 0.022 cm and a gas permeability per 1 cm thickness of 3.2 cc/cm²/sec, were laminated to obtain a laminated sheet with a thickness of 0.088 cm. The recovery time, the amount of blood loss, and the separation strength were determined. The results are shown in Table 1.

Example 6

A filter was prepared in the same manner as in Example 1, except that as a third filter element five sheets of nonwoven fabric, each having a thickness of 0.021 cm and a gas permeability per 1 cm thickness of 3.8 cc/cm²/sec, were laminated to obtain a laminated sheet with a thickness of 0.105 cm. The recovery time, the amount of blood loss, and separation strength were determined. The results are shown in Table 1.

Example 7

A filter was prepared in the same manner as in Example 1, except that as a third filter element two sheets of nonwoven fabric, each having a thickness of 0.023 cm and a gas permeability per 1 cm thickness of 8.8 cc/cm²/sec, were laminated to obtain a laminated sheet with a thickness of 0.046 cm. The recovery time, the amount of blood loss, and separation strength were determined. The results are shown in Table 1.

Example 8

A filter was prepared in the same manner as in Example 1, except that as a third filter element five sheets of nonwoven fabric, each having a thickness of 0.023 cm and a gas permeability per 1 cm thickness of 8.8 cc/cm²/sec, were laminated to obtain a laminated sheet with a thickness of 0.116 cm. The recovery time, the amount of blood loss, and separation strength were determined. The results are shown in Table 1.

Example 9

A filter was prepared in the same manner as in Example 1, except that as a third filter element eight sheets of nonwoven fabric, each having a thickness of 0.023 cm and a gas permeability per 1 cm thickness of 8.8 cc/cm²/sec, were laminated to obtain a laminated sheet with a thickness of 0.185 cm. The recovery time, the amount of blood loss, and separation strength were determined. The results are shown in Table 1.

Example 10

A filter was prepared in the same manner as in Example 1, except that as a third filter element two sheets of nonwoven fabric, each having a thickness of 0.053 cm and a gas permeability per 1 cm thickness of 9.6 cc/cm²/sec, were laminated to obtain a laminated sheet with a thickness of 0.106 cm. The recovery time, the amount of blood loss, and separation strength were determined. The results are shown in Table 1.

Example 11

A filter was prepared in the same manner as in Example 1, except that as a third filter element 10 sheets of polyester screen, each having a thickness of 0.009 cm and a gas permeability per 1 cm thickness of 8.4 cc/cm²/sec, were laminated to obtain a laminated sheet with a thickness of 0.090 cm. The recovery time, the amount of blood loss, and the separation strength were determined. The results are shown in Table 1.

Example 12

A filter was prepared in the same manner as in Example 1, except that as a third filter element four sheets of polyester screen, each having a thickness of 0.030 cm and a gas permeability per 1 cm thickness of 28.8 cc/cm²/sec, were laminated to obtain a laminated sheet with a thickness of 0.120 cm. The recovery time, the amount of blood loss, and separation strength were determined. The results are shown in Table 1.

Example 13

A filter was prepared in the same manner as in Example 1, except that as a third filter element three sheets of polyester screen, each having a thickness of 0.038 cm and a gas permeability per 1 cm thickness of 36.5 cc/cm²/sec, were laminated to obtain a laminated sheet with a thickness of 0.114 cm. The recovery time, the amount of blood loss, and separation strength were determined. The results are shown in Table 1.

Example 14

A filter was prepared in the same manner as in Example 1, except that as a third filter element five sheets of polyester screen, each having a thickness of 0.038 cm and a gas permeability per 1 cm thickness of 36.5 cc/cm²/sec, were laminated to obtain a laminated sheet with a thickness of 0.190 cm. The recovery time, the amount of blood loss, and separation strength were determined. The results are shown in Table 1.

Example 15

A filter shown in FIG. 2 was prepared in the same manner as in Example 1, except for the possession of a sheet-like frame and the features described below. The recovery time, the amount of blood loss, and separation strength were determined. The materials for the inlet port side container and outlet port side container and the filter element were prepared, in the same manner as in Example 1. The polyvinyl chloride resin sheet (n) having the same external dimension as the inlet port side container and the outlet port side container was used as the material for the outlet port side sheet-like frame, of which the inside area was cut out leaving a frame with a width of 3 mm inside the first seal zone (f) The inlet port side sheet-like frame (o) was provided with a frame with a width of 3 mm, on both the inside and outside of the first seal zone (f). A filter element was disposed between the outlet port side sheet-like frame materials and the inlet port side sheet-like frame materials. The first seal zone was formed by high frequency welding. The outlet port side sheet-like frame was covered with the material for the outlet port side container and the inlet port side sheet-like frame was covered with the material for the inlet port side container. Then, the second seal zone was formed by high frequency welding in the same manner as in Example 1. The materials of the container and the sheet-like frame extruding outside the second seal zone were cut out. The results are shown in Table 1.

TABLE 1

| Example | Third element Gas permeability (cc/cm²/sec) | Thickness (cm) | Recovery time (min) | Amount of blood loss (ml) | Separation strength (N/mm) |
|---|---|---|---|---|---|
| 1 | 4.5 | 0.114 | 4.7 | 27.3 | 3.2 |
| 2 | 4.5 | 0.057 | 8.1 | 25.8 | 3.0 |
| 3 | 4.5 | 0.171 | 5.4 | 28.1 | 3.1 |
| 4 | 4.5 | 0.228 | 5.6 | 28.9 | 2.9 |
| 5 | 3.2 | 0.088 | 6.7 | 26.0 | 2.2 |
| 6 | 3.8 | 0.105 | 6.3 | 27.1 | 2.2 |
| 7 | 8.8 | 0.046 | 6.9 | 26.9 | 2.5 |
| 8 | 8.8 | 0.116 | 5.7 | 28.3 | 2.7 |
| 9 | 8.8 | 0.185 | 4.9 | 29.7 | 2.6 |
| 10 | 9.6 | 0.106 | 5.4 | 28.3 | 2.0 |
| 11 | 8.4 | 0.090 | 6.7 | 27.9 | 2.6 |
| 12 | 28.8 | 0.120 | 5.5 | 28.0 | 1.8 |
| 13 | 36.5 | 0.114 | 5.3 | 28.4 | 2.4 |
| 14 | 36.5 | 0.190 | 5.2 | 28.6 | 2.2 |
| 15 | 4.5 | 0.114 | 4.8 | 27.4 | 3.2 |

Comparative Example 1

A filter was prepared in the same manner as in Example 1 except that the third filter element was not used. The recovery time, the amount of blood loss, and separation strength were determined. The results are shown in Table 2.

Comparative Example 2

A filter was prepared in the same manner as in Example 1 except that as a third filter element one sheet of nonwoven fabric having a thickness of 0.019 cm and a gas permeability per 1 cm thickness of 4.5 cc/cm²/sec was laminated. The recovery time, the amount of blood loss, and the separation strength were determined. The results are shown in Table 2.

Comparative Example 3

A filter was prepared in the same manner as in Example 1, except that as a third filter element two sheets of nonwoven fabric, each having a thickness of 0.019 cm and a gas permeability per 1 cm thickness of 4.5 cc/cm²/sec, were laminated to obtain a laminated sheet with a thickness of 0.038 cm. The recovery time, the amount of blood loss, and separation strength were determined. The results are shown in Table 2.

Comparative Example 4

A filter was prepared in the same manner as in Example 1, except that as a third filter element 15 sheets of nonwoven fabric, each having a thickness of 0.019 cm and a gas permeability per 1 cm thickness of 4.5 cc/cm²/sec, were laminated to obtain a laminated sheet with a thickness of 0.285 cm. The recovery time, the amount of blood loss, and separation strength were determined. The results are shown in Table 2.

Comparative Example 5

A filter was prepared in the same manner as in Example 1, except that as a third filter element one sheet of nonwoven fabric having a thickness of 0.023 cm and a gas permeability per 1 cm thickness of 8.8 cc/cm²/sec was laminated. The recovery time, the amount of blood loss, and the separation strength were determined. The results are shown in Table 2.

Comparative Example 6

A filter was prepared in the same manner as in Example 1, except that as a third filter element 12 sheets of nonwoven fabric, each having a thickness of 0.023 cm and a gas permeability per 1 cm thickness of 8.8 cc/cm²/sec, were laminated to obtain a laminated sheet with a thickness of 0.276 cm. The recovery time, the amount of blood loss, and separation strength were determined. The results are shown in Table 2.

Comparative Example 7

A filter was prepared in the same manner as in Example 1, except that as a third filter element one sheet of nonwoven fabric having a thickness of 0.044 cm and a gas permeability per 1 cm thickness of 2.2 cc/cm²/sec was laminated. The recovery time, the amount of blood loss, and the separation strength were determined. The results are shown in Table 2.

Comparative Example 8

A filter was prepared in the same manner as in Example 1, except that as a third filter element two sheets of nonwoven fabric, each having a thickness of 0.044 cm and a gas permeability per 1 cm thickness of 2.2 cc/cm²/sec, were laminated to obtain a laminated sheet with a thickness of 0.088 cm. The recovery time, the amount of blood loss, and separation strength were determined. The results are shown in Table 2.

Comparative Example 9

A filter was prepared in the same manner as in Example 1, except that as a third filter element two sheets of nonwoven fabric, each having a thickness of 0.042 cm and a gas permeability per 1 cm thickness of 0.038 cc/cm²/sec were laminated to obtain a laminated sheet with a total thickness of 0.042 cm. The recovery time, the amount of blood loss, and the separation strength were determined. The results are shown in Table 2.

Comparative Example 10

A filter was prepared in the same manner as in Example 1, except that as a third filter element three sheets of nonwoven fabric, each having a thickness of 0.042 cm and a gas permeability per 1 cm thickness of 0.038 cc/cm$^2$/sec were laminated to obtain a laminated sheet with a total thickness of 0.126 cm. The recovery time, the amount of blood loss, and the separation strength were determined. The results are shown in Table 2.

Comparative Example 11

A filter was prepared in the same manner as in Example 1, except that instead of the third filter element five sheets of nonwoven fabric, each having a thickness of 0.042 cm and a gas permeability per 1 cm thickness of 0.038 cc/cm$^2$/sec were laminated to obtain a laminated sheet with a total thickness of 0.208 cm. The recovery time, the amount of blood loss, and the separation strength were determined. The results are shown in Table 2.

Comparative Example 12

A filter was prepared in the same manner as in Example 1, except that one sheet of polyolefin screen, with one side of the opening of 2.8 mm, a fiber diameter of 500 μm, and an opening ratio of 77%, was laminated instead of a third filter element to provide a thickness of 0.090 cm. The recovery time, the amount of blood loss, and separation strength were determined. The gas permeability of the screen per 1 cm thickness could not be measured because the value was too large to determine. Based on the number of laminated sheets and the measured area of the test specimen, the gas permeability estimated to be larger than 100 cc/cm$^2$/sec. The results own in Table 2.

second filter element, a total 27 sheets of nonwoven fabric consisting of one sheet of nonwoven fabric (2) with an average fiber diameter of 1.7 μm and a density of 66 g/m$^2$, 25 sheets of nonwoven fabric (3) with an average fiber diameter of 1.2 μm and a density of 40 g/m$^2$, and one sheet of nonwoven fabric (2) were laminated in that order. Then, one sheet of the nonwoven fabric (1) was laminated as the third filter element, with the total of 32 sheets being laminated. The gas permeability per 1 cm thickness of the third filter element was 4.5 cc/cm$^2$/sec and the thickness was 0.019 cm. The laminated filter element was cut into a rectangle of 85 mm×68 mm to be used as the filter element (c). The flexible container materials (b, d) and the filter element (c) were layered as shown in FIG. 1, and welded by high frequency welding to form the first seal zone (f) with a length of 3 mm. No second seal zone was formed to reduce the time required for the test. 15 filters prepared in this manner was divided into three groups. The thickness of the composite material layer, separation strength, and fracture time were determined using five filters of each group. The average of the results obtained for five filters is shown in Table 3.

Example 17

A filter was prepared in the same manner as in Example 1, except for using two sheets of nonwoven fabric (1) as the third filter element. The same test as in Example 16 was carried out. The average of the results obtained for five filters is shown in Table 3. The gas permeability per 1 cm thickness of the third filter element was 4.5 cc/cm$^2$/sec and the thickness was 0.038 cm.

TABLE 2

| Comparative Example | Third element | | Recovery time (min) | Amount of blood loss (ml) | Separation strength (N/mm) |
| --- | --- | --- | --- | --- | --- |
| | Gas permeability (cc/cm$^2$/sec) | Thickness (cm) | | | |
| 1 | — | 0 | 17.4 | 24.5 | 0.9 |
| 2 | 4.5 | 0.019 | 13.9 | 25.0 | 1.2 |
| 3 | 4.5 | 0.038 | 11.1 | 25.3 | 1.4 |
| 4 | 4.5 | 0.285 | 6.0 | 30.1 | 1.2 |
| 5 | 8.8 | 0.023 | 10.5 | 26.4 | 1.0 |
| 6 | 8.8 | 0.276 | 5.2 | 30.8 | 1.3 |
| 7 | 2.2 | 0.044 | 12.7 | 25.5 | 2.2 |
| 8 | 2.2 | 0.088 | 12.5 | 26.3 | 2.0 |
| 9 | 0.38 | 0.042 | 13.4 | 29.0 | 0.9 |
| 10 | 0.38 | 0.126 | 16.1 | 31.0 | 1.0 |
| 11 | 0.38 | 0.208 | 18.7 | 33.8 | 0.9 |
| 12 | >100 | 0.090 | 5.1 | 28.6 | 0.9 |

Example 16

An inlet port side container material (b) having an inlet port (a) and an outlet port side container material (d) having an outlet port (e), each having a dimension of 120 mm×100 mm, as shown in FIG. 1, were prepared by combining a blood inlet port (a) and a blood outlet port (e), each made of a polyvinyl chloride resin formed by injection molding, with sheets (b) and (d) of soft polyvinyl chloride resin, each having a hole at the location of adherence, by means of high frequency welding. A laminate of the following sheets of nonwoven polyester fabric was used as the filter element (c). Four sheets of nonwoven fabric (1) with an average fiber diameter of 12 μm and a density of 30 g/m$^2$ were used as the first filter element. As the Example 18

A filter was prepared in the same manner as in Example 1, except for using four sheets of nonwoven fabric (1) as the third filter element. The same test as in Example 16 was carried out. The average of the results obtained for five filters is shown in Table 3. The gas permeability per 1 cm thickness of the third filter element was 4.5 cc/cm$^2$/sec and the thickness was 0.076 cm.

Example 19

A filter was prepared in the same manner as in Example 1, except for using six sheets of nonwoven fabric (1) as the third filter element. The same test as in Example 16 was carried out. The average of the results obtained for five filters is shown in Table 3. The gas permeability per 1 cm thickness of the third filter element was 4.5 cc/cm²/sec and the thickness was 0.114 cm.

Example 20

A filter was prepared in the same manner as in Example 1, except for using eight sheets of nonwoven fabric (1) as the third filter element. The same test as in Example 16 was carried out. The average of the results obtained for five filters is shown in Table 3. The gas permeability per 1 cm thickness of the third filter element was 4.5 cc/cm²/sec and the thickness was 0.0152 cm.

Example 21

A filter was prepared in the same manner as in Example 1, except for using four sheets of nonwoven fabric (1) as the third filter element and increasing the number of sheets of nonwoven fabric (3) for the second filter element to 32 sheets. The same test as in Example 1 was carried out. The average of the results obtained for five filters is shown in Table 3. The gas permeability per 1 cm thickness of the third filter element was 4.5 cc/cm²/sec and the thickness was 0.076 cm.

Example 22

Four sheets of the nonwoven fabric (1) were laminated as the first filter element, 27 sheets in total consisting of one sheet of nonwoven fabric (2), 25 sheets of nonwoven fabric (3), and one sheet of nonwoven fabric (2) were laminated as the second filter element, and four sheets of the nonwoven fabric (1) were laminated as the third filter element, with the total of 35 sheets being laminated. The gas permeability per 1 cm thickness of the third filter element was 4.5 cc/cm²/sec and the thickness was 0.076 cm. The laminated filter element was cut into a rectangle of 85 mm×68 mm to be used as the filter element. The filter element was sandwiched between an inlet port side sheet-like frame that is cut into a frame-shape with an external dimension of 85 mm×68 mm and internal dimension of 69 mm×52 mm and an outlet port side sheet-like frame that is cut into a frame-shape with an external dimension of 120 mm×100 mm and internal dimension of 69 mm×52 mm. The layered sheet-like frames were attached to the filter element by high frequency welding to provide a first seal zone with a width of 3 mm. Then, the outlet port side sheet-like frame was placed between an inlet port side container material (120 mm×100 mm) with an inlet port and an outlet port side container material (120 mm×100 mm) with an outlet port and welded by high frequency welding to provide a second seal zone with an internal dimension of 91 mm×74 mm and a width of 3 mm. 15 filters prepared in this manner was divided into three groups. The thickness of the composite material layer, separation strength, and fracture time were determined for five filters of each group. The average of the results obtained for five filters is shown in Table 3.

TABLE 3

| | Composite material layer | | | |
| --- | --- | --- | --- | --- |
| Example | Thickness of on inlet port side (mm) | Thickness of on outlet port side (mm) | Separation strength (N/mm) | Fracture time (sec) |
| 16 | 0.183 | 0.182 | 2.61 | 1024 |
| 17 | 0.282 | 0.183 | 2.58 | 978 |
| 18 | 0.278 | 0.241 | 2.88 | 1545 |
| 19 | 0.287 | 0.256 | 2.74 | 1285 |
| 20 | 0.278 | 0.316 | 2.71 | 1315 |
| 21 | 0.293 | 0.324 | 3.05 | 2064 |
| 22 | 0.355 | 0.355 | 2.21 | 673 |

Comparative Example 13

A filter was prepared without using a third filter element, without using the nonwoven fabric (1) on the outlet port side, and employing high frequency welding conditions for providing the composite material layer with a thickness of 0.1 mm or less. The method of Example 1 was followed for all other filter preparation conditions. Then, the same tests as in Example 1 were carried out. The average of the results obtained for five filters is shown in Table 4.

Comparative Example 14

A commercially available frame welding type filter was obtained to measure the thickness of composite material layer, the separation-breaking strength, and the fracture time. This filter had sheet-like frames disposed on both the inlet port side and the outlet port side as shown in FIG. 2, with only the outlet port side sheet-like frame being joined with the container to form a second seal zone. The thickness of the composite material layer in the outlet port side sheet-like frame forming the second seal zone was less than 0.15 mm. As described in connection with the method of measurement, to make it possible to carry out these tests, a sheet of soft polyvinyl chloride, which is the same material as the sheet-like frame, was caused to adhere to the sheet-like frame prior to the measurement of the separation-breaking strength and the fracture time. The results are shown in Table 4.

TABLE 4

| Comparative Example | Composite material layer | | Separation-breaking strength (N/mm) | Fracture time (sec) |
| --- | --- | --- | --- | --- |
| | Thickness of on inlet port side (mm) | Thickness of on outlet port side (mm) | | |
| 13 | 0.243 | 0.004 | 1.57 | 8 |
| 14 | 0.250 | 0.132 | 0.77 | 10 |

INDUSTRIAL APPLICABILITY

As described above, a flexible blood processing filter, in which the blood flow may not be affected when the filter element is caused to adhere to the outlet port side container due to the positive pressure on the inlet port side or the negative pressure on the outlet port side during filtration operation, can be provided by selecting the gas permeability and the thickness of the third filter element. In addition, a flexible blood processing filter with superior pressure resistance, separation resistance, and sufficient strength against the pressure during filtration or the stress during centrifugation can be provided by forming a composite material layer with a thickness of 0.15-0.4 mm.

The invention claimed is:

1. A blood processing filter comprising a flexible container, which has a blood inlet port and a blood outlet port, and a sheet-like filter element for removing undesirable components from blood, wherein,
    the blood inlet port is separated from the outlet port by the filter element, a first seal zone is formed by integrating a section near a periphery of the sheet-like filter element with the flexible container over an entire circumference of the flexible container,
    a second seal zone is formed by integrating a blood inlet port side section of the flexible container with a blood outlet port side section of the flexible container over an entire outside circumference of the first seal zone,
    an unsealed zone disposed between the first seal zone and the second seal zone, and
    a cross-section of the first seal zone comprises at least five layers from the blood inlet port side to the blood outlet port side, said five layers consist of
    a layer consisting only of a blood inlet port side flexible container material,
    a blood inlet port side composite material layer wherein the blood inlet port side flexible container material is mixed with a filter element material, a molten container material invading fiber voids of the filter element and the fibers being embedded by the material of the container,
    a layer consisting only of molten filter element material,
    a blood outlet port side composite material layer wherein a blood outlet port side flexible container material is mixed with the filter element material, the molten container material invading the fiber voids of the filter element and the fibers being embedded by the material of the container, and
    a layer consisting only of a blood outlet port side flexible container material,
    wherein both the blood inlet port side composite material layer and the blood outlet port side composite material layer have a thickness between 0.15 mm and 0.4 mm.

2. The blood processing filter according to claim 1, wherein the filter element comprises a first filter element for removing aggregate from blood and a second filter element arranged downstream of the first filter element to remove leukocytes.

3. The blood processing filter according to claim 1, wherein the filter element comprises a third filter element disposed between the second filter element and the blood outlet port side of the flexible container for preventing adhesion of the blood outlet port side of the flexible container to the second filter element.

4. The blood processing filter according to claim 2, wherein the blood inlet port side composite material layer contains the material of the blood inlet port side of the flexible container or a sheet-like frame and the first filter element as main components.

5. The blood processing filter according to claim 3, wherein the blood outlet port side composite material layer contains the material of the blood outlet port side of the flexible container and the third filter element as main components.

6. The blood processing filter according to claim 3, wherein the third filter element has a gas permeability per 1 cm thickness of 3-40 cc/cm$^2$/sec and a thickness of 0.04-0.25 cm.

7. The blood processing filter according to claim 1, wherein the flexible container is formed from a sheet-like formed material.

8. The blood processing filter according to claim 1, wherein the flexible container is formed from a cylindrical formed material.

9. The blood processing filter according to claim 1, wherein the blood inlet port and blood outlet port made from formed parts are liquid-tightly joined with the flexible container.

10. The blood processing filter according to claim 1, wherein the flexible container is formed from soft polyvinyl chloride.

11. The blood processing filter according to claim 1, wherein the blood inlet port and blood outlet port are formed from soft polyvinyl chloride.

12. The blood processing filter according to claim 1, wherein the flexible container is formed from polyolefin.

13. The blood processing filter according to claim 12, wherein the blood inlet port and blood outlet port are formed from polyolefin.

14. A system for removing leukocytes from blood, comprising:
    a centrifuge; and
    the blood processing filter according to claim 1.

* * * * *